US010721392B2

United States Patent
Agell et al.

(10) Patent No.: US 10,721,392 B2
(45) Date of Patent: Jul. 21, 2020

(54) METHOD AND A SYSTEM FOR EYE TRACKING

(71) Applicant: Stichting IMEC Nederland, Eindhoven (NL)

(72) Inventors: Carlos Agell, Eindhoven (NL); Pierluigi Casale, Leuven (BE)

(73) Assignee: Stichting IMEC Nederland, Eindhoven (NL)

(*) Notice: Subject to any disclaimer, the term of this patent is extended or adjusted under 35 U.S.C. 154(b) by 7 days.

(21) Appl. No.: 15/651,445

(22) Filed: Jul. 17, 2017

(65) Prior Publication Data
US 2018/0027176 A1 Jan. 25, 2018

(30) Foreign Application Priority Data
Jul. 19, 2016 (EP) .................................. 16180066

(51) Int. Cl.
| | | |
|---|---|---|
| H04N 5/232 | (2006.01) | |
| A61B 3/113 | (2006.01) | |
| A61B 5/0496 | (2006.01) | |
| G06F 3/01 | (2006.01) | |
| G06T 7/73 | (2017.01) | |

(Continued)

(52) U.S. Cl.
CPC ......... *H04N 5/23219* (2013.01); *A61B 3/113* (2013.01); *A61B 5/0496* (2013.01); *G06F 3/013* (2013.01); *G06F 3/017* (2013.01); *G06K 9/0061* (2013.01); *G06T 7/20* (2013.01); *G06T 7/74* (2017.01); *H04N 5/23241* (2013.01); *A61B 3/112* (2013.01); *G06T 2207/10016* (2013.01); *G06T 2207/30041* (2013.01)

(58) Field of Classification Search
CPC .... G06T 7/74; G06T 7/20; G06T 7/00; G06T 2207/30041; G06T 2207/10016; H04N 5/23219; H04N 5/23241; G06K 9/0061; G06F 3/017; G06F 3/013; A61B 3/113; A61B 5/0496; A61B 3/112
USPC .......................................... 345/156; 348/158
See application file for complete search history.

(56) References Cited

U.S. PATENT DOCUMENTS

| | | | |
|---|---|---|---|
| 2005/0099601 A1 | 5/2005 | MacDougall et al. | |
| 2008/0104415 A1* | 5/2008 | Palti-Wasserman | G06F 21/32 713/186 |

(Continued)

OTHER PUBLICATIONS

"Eye Movement Tracking Device", Department of Electrical Engineering, Kate Gleason College of Engineering at the Rochester Institute of Technology, Project No. P09004. http://edge.rit.edu/edge/P09004/public/Home#_Concept_Development.

(Continued)

Primary Examiner — Tung T Vo
(74) Attorney, Agent, or Firm — Moser Taboada (57) ABSTRACT

According to an aspect of the present inventive concept there is provided a method for eye tracking, comprising: capturing a sequence of digital images of an eye of a user; outputting data including said sequence of images to an image processing unit; processing said data by the image processing unit to determine a sequence of positions of the eye, each position being indicative of a gaze direction, acquiring biosignal data representing an activity of the eye; and in response to detecting closing of the eye based on the acquired biosignal data, pausing at least one of said capturing, said outputting and said processing. A system for implementing the method is also disclosed.

16 Claims, 4 Drawing Sheets

(51) Int. Cl.
*G06K 9/00* (2006.01)
*G06T 7/20* (2017.01)
*A61B 3/11* (2006.01)

(56) References Cited

U.S. PATENT DOCUMENTS

| | | | |
|---|---|---|---|
| 2011/0121976 A1* | 5/2011 | Johns | A61B 3/113 340/576 |
| 2014/0313129 A1 | 10/2014 | Elvesjö et al. | |
| 2015/0301594 A1 | 10/2015 | Kitazawa et al. | |
| 2016/0022167 A1* | 1/2016 | Simon | A61B 5/04842 600/301 |
| 2016/0025971 A1* | 1/2016 | Crow | G02B 27/0093 345/156 |
| 2016/0077547 A1* | 3/2016 | Aimone | G06F 3/012 345/8 |
| 2017/0103574 A1* | 4/2017 | Faaborg | G02B 27/0172 |
| 2017/0147859 A1* | 5/2017 | Zhang | G02B 27/0093 |

OTHER PUBLICATIONS

"Electrooculographic (EOG) Eye Tracking", Oculus Rift DK Developers Forum. https://forums.oculus.com/developer/discussion/893/electrooculographic-eog-eye-tracking.

"Research about Brain-Machine Interface", Matsuno Lab Kyoto University—BMI. http://www.mechatronics.me.kyoto-u.ac.jp/modules/kenkyu/index.php?content_id=23&ml_lang=en.

Picot et al., "Comparison between EOG and High Frame Rate Camera for Drowsiness Detection", IEEE Workshop on Applications of Computer Vision (WAVC), Dec. 7-8, 2009.

Hirvonen et al., "Simultaneous Electro-Oculography and Video-Oculography Recordings", European Conference on Eye Movements, 2011. http://congress.utu.fi/ecem11/methods/Hirvonen.htm.

Chaudhuri et al., "Video & EOG Based Investigation of Pure Saccades in Human Subjects", IEEE Proceedings of 4th International Conference on Intelligent Human Computer Interaction, Kharagpur, India, Dec. 27-29, 2012.

Du et al., "Online Vigilance Analysis Combining Video and Electrooculography Features", International Conference on Neural Information Processing (ICONIP) 2012, Part V, Lecture Notes in Computer Science (LNCS), vol. 7667, pp. 447-454, 2012.

Majaranta et al., "Eye Tracking and Eye-Based Human-Computer Interaction", Advances in Physiological Computing, Human-Computer Interaction Series, Springer-Verlag London 2014.

Extended European Search Report dated Jan. 24, 2017 for Application No. 16180066.9.

* cited by examiner

METHOD AND A SYSTEM FOR EYE TRACKING

CROSS-REFERENCE TO RELATED APPLICATION

This application claims the benefit of priority to European Patent Application No. 16180066.9 filed Jul. 19, 2016, and is incorporated herein by reference in its entirety.

FIELD OF THE INVENTION

The present inventive concept relates to a method and a system for eye tracking.

BACKGROUND

In image-based eye tracking an image capturing device, such as a digital camera or an imaging sensor, acquires a digital image of the eye and processes the image to estimate gaze direction, pupil size or other eye-related features. Image processing techniques for eye tracking may be expensive in terms of computation time, power consumption, memory footprint, etc. Additionally, eye-related events may be comparably "fast" or "brief". Hence for accurate eye tracking, image acquisition and image processing needs to be performed at a correspondingly high frame rate. Some applications of eye tracking require real time or near-real time performance as the eye tracking may be used as a user-interaction method, so low latency is important.

SUMMARY

An objective of the present inventive concept is to enable improved image-based eye tracking. Additional objectives include enabling a more power efficient, more memory efficient and/or more computationally efficient eye tracking. Further and alternative objectives may be understood from the following.

According to a first aspect of the present inventive concept there is provided a method for eye tracking, comprising:

capturing a sequence of digital images of an eye of a user;

outputting data including said sequence of images to an image processing unit;

processing said data by the image processing unit to determine a sequence of positions of the eye, each position being indicative of a gaze direction, acquiring biosignal data representing an activity of the eye; and in response to detecting closing of the eye based on the acquired biosignal data, pausing at least one of said capturing, said outputting and said processing.

The inventive concept is based on the insight that an improved eye tracking is possible by taking an activity of the eye into account during an eye tracking process. More specifically, detecting when the eye is closed makes it possible to pause at least a part of the eye tracking process. By way of example, eye blinks may occur 15 to 20 times per minute in average with durations between 300 and 400 ms. Thus, the eye may be blocked between approximately 7.5% and 13% of the time during a given time interval.

When the eye is closed, determining a position of the eye by image analysis will be prevented. Accordingly, for the purpose of eye tracking, capturing images while the eye is closed as well as storing and processing data of such images may be considered inefficient in terms of power usage, memory usage and processing cycles. The inventive method removes or at least reduces one or more of these issues.

A further advantage of the inventive method is that it may be ascertained that an image to be processed is indeed of an eye wherein waste of computational resources due to non-convergence of imaging processing techniques may be avoided.

Since the method enables power-saving, the method lends itself for use in a relatively compact and power-efficient user-wearable device. For instance, such a device may not need charging very often or the device may be provided with small-size and light batteries.

In this context, detecting closing of the eye means detecting that the eye begins to close or changes from being open to being closed. An eye being closed implies that eye lids occlude the eye ball. From an image capturing point of view, closing of the eye means that the iris and pupil are partially or totally occluded due to motion of the eye lids. From a biosignal acquisition point of view, closing of the eye means activation of the muscle that enables motion of the eye lids to occlude the eye ball.

An eye blink as used herein thus refers to a movement of the eye lids for closing the eye and opening the eye again. The start and end of the eye blink may be a position of the eye lids which covers the eye ball to such a degree that features of the eye ball cannot be reliably extracted from an image of the eye.

By performing an act in response to detecting closing of the eye is hereby meant initiating performing of said act upon or when closing of the eye is detected.

The act of "pausing at least one of said capturing, said outputting and said processing" may here be construed as setting at least one of said capturing, said outputting and said processing into a (respective) paused state. A paused state of the capturing implies that no image capturing is performed. A paused state of said outputting implies that no data including said sequence of images is output to the image processing unit. A paused state of said processing implies that no processing of said data is performed by the image processing unit.

A method including pausing of said capturing is particularly advantageous in a (near) real-time eye tracking scenario wherein the method enables (near) real-time control of the image capturing on the basis of the acquired biosignal data. This applies correspondingly to a method including pausing of said outputting wherein the method enables (near) real-time control of the output of data on the basis of the acquired biosignal data.

A method including pausing of said post-processing (possibly not including pausing of said capturing or said outputting) is particularly advantageous in a post-processing scenario wherein images are captured and biosignals are acquired and subsequently post-processed to track/analyze the eye on the basis of the captured images. Such a method enables the image processing during post-processing to be paused in response to detecting closing of the eye based on the acquired biosignal data. The image processing may be paused while the eye is closed wherein image processing of digital images depicting a closed eye may be skipped. Power required during the image processing may thereby be reduced.

A position of the eye, as used herein, refers to a position, or equivalently the orientation or the rotation, of the eye in relation to a frame of reference, preferably in relation to the head of the user (i.e. a frame of reference having a fixed relationship with respect to the head). The position of the eye determines the gaze direction in relation to the frame of reference.

Each determined position of the eye may be determined based on data of a respective single image of the captured sequence of digital images.

Processing said data by the image processing unit may include identifying a set of one or more image features of the eye. Features may include, in addition to position of the eye, the location of the center of the pupil, the size of the pupil, the speed of motion of the pupil, the area of the pupil, identification of features on the iris, evolution of tone of the iris over time, and analysis of blood vessels in the sclera or other features that can be extracted from image analysis on images of the eye. The set or combination of one or more image features may be indicative of a higher level variable, such as gaze, concentration, etc.

The acts of capturing, outputting and processing may form part of an eye tracking process. The eye tracking process may include further acts such as generation, outputting and/or recording of data representing the sequence of positions of the eye.

The method may further comprise returning, to an active state, each of said at least one of: said capturing, said outputting and said processing being in a paused state. Thereby each paused act (i.e. each act being in a paused state) of said at least one of said capturing, said outputting and said processing may be resumed. This is particularly advantageous for pausing the eye tracking process during eye blinks and resuming the eye tracking process once the eye is open again at the end of the blink.

An active state of the act of capturing implies that image capturing is resumed. An active state of the act of outputting implies that outputting of data including captured images to the image processing unit is resumed. An active state of the act of processing implies that processing, by the image processing unit, of data including captured images is resumed.

The method may comprise, in response to detecting closing of the eye based on the acquired biosignal data, setting said capturing to a paused state and subsequently returning said capturing to an active state.

The method may comprise, in response to detecting closing of the eye based on the acquired biosignal data, setting said outputting to a paused state and subsequently returning said outputting to an active state.

The method may comprise, in response to detecting closing of the eye based on the acquired biosignal data, setting said processing to a paused state and subsequently returning said processing to an active state.

According to one embodiment, said returning of an act to an active state includes transitioning said act from a paused state to a waiting state and transitioning said act from the waiting state to the active state. Transitioning a paused act to an intermediate waiting state enables putting the eye tracking process in prepared state for resuming the eye tracking.

A waiting state of the image capturing may include initializing an image capturing device to a "ready" condition. There by allowing image capturing to be quickly resumed when transitioning to the active state.

A waiting state of the outputting of data may include clearing and/or allocating storage areas for image data and/or initializing and/or reserving a data bus for communication with the image processing unit. There by allowing outputting of data to be quickly resumed when transitioning to the active state.

A waiting state of the processing of the image processing unit may include initializing registers, variables and/or control loops used for the processing. There by allowing image processing to be quickly resumed when transitioning to the active state.

The transitioning from the paused state to the waiting state may be performed after a preset time delay from said pausing. The duration of the preset time delay may be based on a priori knowledge of an average duration of a blink. Hence, the time instant of a transition from a paused to a waiting state may be efficiently determined in a reliable manner based on a timer. The preset time delay may hence be set such that there is sufficient time for the eye tracking process to prepare for being resumed again once the eye re-opens. The preset time delay may be based on a response/start-up time of the hardware used for the eye tracking process.

The transitioning from the waiting state to the active state may be performed in response to detecting opening of the eye based on the acquired biosignal data. Thereby, the acts of the eye-tracking method which were paused in response to detecting closing of the eye may be quickly resumed by transitioning from the respective waiting state(s) when the biosignal data indicates that the eye is re-opening.

By detecting opening of the eye is hereby meant detecting that the eye begins to open or changes from being closed to being open.

According to one embodiment, returning of an act to an active state is performed in response to detecting opening of the eye based on the acquired biosignal data. This embodiment enables a simple implementation of resuming the acts of the eye-tracking process which were paused in response to detecting closing of the eye by directly transitioning from a respective paused state to a respective active state in response to detecting opening of the eye.

According to one embodiment said act of returning to an active state is performed after a preset time delay from said act of pausing. This embodiment enables a simple implementation of resuming the acts of the eye-tracking process which were paused in response to detecting closing of the eye by directly transitioning from a respective paused state after a preset time delay. The duration of the preset time delay may be based on a priori knowledge of an average length of a blink. Hence, the time instant of a transition from a paused to a waiting state may be efficiently determined in a reliable manner based on a timer.

According to a second aspect of the present inventive concept there is provided a system for eye tracking, comprising:

an image capturing device configured to capture a sequence of digital images of an eye;

an image processing unit configured to receive data including said sequence of images from the image capturing device and determine a sequence of positions of the eye, each position being indicative of a gaze direction;

a biosignal acquisition unit configured to acquire biosignal data representing an activity of the eye;

a biosignal processing unit configured to receive the biosignal data and detect closing of the eye based on the acquired biosignal data; and a control unit configured to, in response to the biosignal processing unit detecting closing of the eye, outputting a control signal for pausing at least one of: an image capture operation of the image capturing device, an image processing operation of the image processing unit, and a transfer of data including said sequence of images between the image processing unit and the image capturing device.

This aspect may generally present the same or corresponding advantages as the former aspect wherein reference is made to the above discussion.

By image capturing device is hereby meant any device having the function of imaging, in the form of digital image data. The image capturing device may be a digital camera or any imaging sensor (complementary metal-oxide-semiconductor (CMOS) or a charge-coupled device (CCD)) with digital readout.

The image processing unit means any unit being capable of performing digital image processing. The unit may be implemented as a dedicated image processing unit including circuitry dedicated to perform the functions of the image processing unit. The circuit may be a digital logic circuit. The circuit may be implemented in an integrated circuit such as a chipset. The circuit may also be implemented in a field programmable gate array (FPGA) or an application specific integrated circuit (ASIC). The image processing unit may also be implemented in a general-purpose processing unit, such as a microprocessor, e.g. a central processing unit (CPU), which may be provided with a set of software instructions for performing the processing operations.

By biosignal acquisition unit is here meant any unit being capable of acquiring analog biosignals by electrical measurements on the user, preferably via a set of skin electrodes. The biosignal acquisition unit may further convert the analog biosignals to digital samples. The unit may be a dedicated sensor circuit, an application specific integrated circuit (ASIC) or a block of a higher functionality system, such as a system on chip (SoC) or system in package (SiP).

By biosignal processing unit is here meant any unit being capable of processing the biosignal data and detecting closing of the eye based on the acquired biosignal data. The unit may be implemented as a dedicated hardware biosignal processing unit including circuitry dedicated to perform the functions of the biosignal processing unit. The circuit may be a digital logic circuit. The circuit may be implemented in an integrated circuit such as a chipset. The circuit may also be implemented in a FPGA or an ASIC. The biosignal processing unit may also be implemented in circuitry being shared with the image processing unit. The biosignal processing unit may also be implemented in software residing in a general-purpose processing unit, such as a microcontroller (MCU), a microprocessor, e.g. a CPU, which may be provided with a set of software instructions for performing the processing operations. The biosignal processing unit may be implemented in a same processing unit as the image processing unit.

The term control unit, as used herein, refers to any unit being capable of outputting a control signal for pausing said at least one of the image capture operation, the image processing operation and the transfer of data. The unit may be implemented as a dedicated control unit including circuitry dedicated to perform the functions of the control unit. The circuit may be a digital logic circuit. The circuit may be implemented in an integrated circuit such as a chipset. The circuit may also be implemented in a FPGA or an ASIC. The control unit may also be implemented in circuitry being shared with the biosignal processing unit and/or the image processing unit. The control unit may also be implemented in a general-purpose processing unit, such as a microprocessor, e.g. a central processing unit (CPU), which may be provided with a set of software instructions for performing the processing operations. The control unit may be implemented in a same processing unit as the biosignal processing unit and/or the image processing unit.

The control signal output by the control unit may be an analog or a digital control signal transmitted from the control unit. The control signal may also include the setting of a control flag or the like in a register accessible by the other units of the system and allowing said other units to determine when their respective operation should be paused.

The control unit may be further configured to output at least one control signal for returning to an active state each of the image capture operation, the image processing operation, and the transfer of data being in a paused state.

According to one embodiment the control unit is configured to output said at least one control signal after a preset time delay from said output of the control signal for pausing or in response to the biosignal processing unit detecting opening of the eye based on the acquired biosignal data.

According to another embodiment the control unit is further configured to output:

a first control signal for transitioning each of the image capture operation, the image processing operation, and the transfer of data being in a paused state to a waiting state; and a second control signal for transitioning each of the image capture operation, the image processing operation, and the transfer of data being in the waiting state to the active state.

The control unit may be configured to output the first control signal after a preset time delay from said output of the control signal for pausing.

The control unit may be configured to output the second control signal (subsequent to the first control signal and) in response to the biosignal processing unit detecting opening of the eye based on the acquired biosignal data.

According to one embodiment the system further comprises a structure adapted to be head-mounted on the user, wherein the image capturing device and the biosignal acquisition unit are supported by the structure. Since the system is arranged to save processing power and generally is power-saving, the system facilitates arrangement as a wearable. For instance, the system may not need charging very often or the system may be provided with small-size and light batteries.

According to one embodiment the biosignal acquisition unit includes a set of skin electrodes adapted to be arranged in an eye region of the user, and arranged along a longitudinal axis running in a direction of eye lid movement.

In many applications, e.g. when eye tracking is used as a user-interaction method, the system may need to have real time or near-real time performance.

According to one embodiment, the image capturing device, the image processing unit, the biosignal acquisition unit and the biosignal processing unit perform in real time. This implies that the power saving enabled by pausing at least one of: an image capture operation of the image capturing device, an image processing operation of the image processing unit, and a transfer of data including said sequence of images between the image processing unit and the image capturing device is effective as the operations are performed in real time.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION

Figure 1:
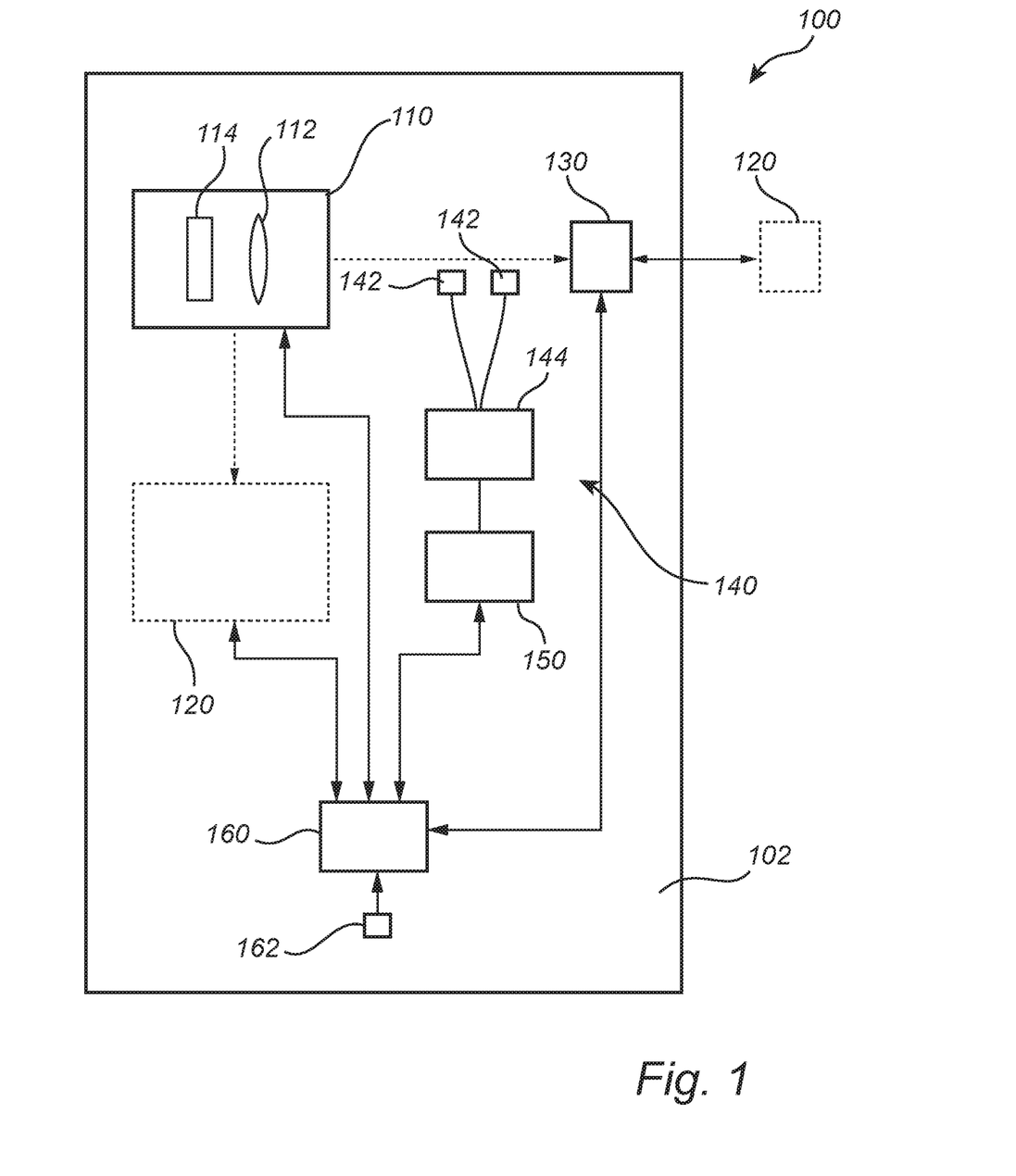
FIG. 1 is a schematic view of a system for image-based eye tracking.

Referring now to FIG. 1, a system 100 for image-based eye tracking will be discussed. Eye tracking may be used for multiple applications, such as in research of the human visual system or as input for controlling interaction between a human and a computing device. For instance, the system 100 may at least partly be implemented in a wearable device, e.g. in a head-mounted structure such as goggles, or other eyewear that are worn by a user in applications ranging from augmented reality, virtual reality or biosignal acquisition and processing. A pair of goggles may be provided with two systems 100 for image-based eye tracking, one system 100 for each eye. However, two such systems 100 may at least partly share components, for instance, for processing acquired data. Below, only a single system 100 will be described.

The system 100 may comprise an image capturing device 110. The image capturing device 110 may be implemented as a digital camera, which may be integrated in a wearable device. For instance, the camera may be arranged in the head-mounted structure worn by the user, set up to acquire images from the user's eyes in a close range. However, the image capturing device 110 may also be arranged at a distance from the user. For instance the image capturing device 110 may be formed by a digital camera integrated in or connectable to a desktop computer monitor, a laptop, a mobile phone, a tablet computer or some other portable computing device. Other examples include a TV or a video game console.

The image capturing device 110 may comprise an optical system 112 and an image sensor 114. The optical system 112 may be arranged to image an object onto the image sensor 114. The optical system 112 may be pre-configured to be adapted for imaging an eye in close range. For instance, a distance between the optical system 112 and an eye may be well-known in advance, if the image capturing device 110 is integrated in the head-mounted structure, such as goggles.

The image sensor 114 may comprise an array of photo-sensitive areas and may be arranged to record an image by means of the photo-sensitive areas being controlled to output signals representative of accumulated incoming light.

The image sensor 114 may be a complementary metal-oxide-semiconductor (CMOS) image sensor or a charge-coupled device (CCD) image sensor.

The image capturing device 110 may be configured to capture a sequence of digital images of an eye. The images may be arranged to image the eye, and possibly a small area around the eye in order to allow determining an eye position of a user which may be indicative of a gaze direction and possibly other eye features providing useful information, such as pupil location, pupil area, pupil speed, unique iris identification information, and reaction time to optical stimuli.

The system 100 may further comprise an image processing unit 120. The image processing unit 120 may be configured to receive data including the sequence of digital images from the image capturing device 110.

The image processing unit 120 may be a logic digital block of a higher level entity such as an ASIC, SiP, SoC, intrinsically connected to the image sensor 114, e.g. by sharing a data bus.

The image processing unit 120 may be directly connected to the image sensor 114, e.g. by being mounted on a common printed circuit board or connected through a wired connection to the image sensor 114.

Alternatively, the image processing unit 120 may be arranged remotely to the image capturing device 110. For instance, the image processing unit 120 may be arranged in a desktop computer, a laptop, a TV, a video game console or in a portable computing device, which may also be carried or worn by the user, such as in a mobile phone or a tablet computer. In such case, the system 100 may further comprise a transmitter 130 for communicating between the image capturing device 110 and the image processing unit 120. For instance, the transmitter 130 may be arranged for wireless communication, e.g. using Bluetooth®/WiFi® or another wireless protocol, with an external unit in which the image processing unit 120 may be arranged.

The image processing unit 120 may be configured to process the sequence of digital images in order to determine a sequence of positions, orientations, rotations and other features of the eye. The image processing unit 120 may, for instance, determine a position of the pupil and/or a position of the iris, the area of the pupil, its perimeter, or the ratio between areas of iris and pupil which may in turn be used to determine a gaze direction of the user, a reaction of the user to external stimuli or the eye speed, among other eye-related features.

The processing by the image processing unit 120 may include further eye feature extraction. For instance, pupil size and iris measurements may be performed for each digital image. Also, based on the sequence of digital images, eye feature extraction may include eye movement, pupil variation, pupil velocity, etc.

The features extracted by the image processing unit 120 may be stored in a memory for future analysis and/or may be reported, e.g. to a controller for interpreting the extracted features in providing a human-computer interface.

The image processing unit 120 may need to perform relatively extensive image processing of each image in order to extract the desired features. The image processing performed by the processing unit 120 may thus be based on an assumption that an eye is imaged in each digital image in order to speed up processing. Therefore, if the eye is closed in a captured image, the image processing may take longer to converge or not converge to any final valid result, which means that resources (processing time and cycles, memory) may be wasted in processing of a non-useful image.

The system 100 may further comprise a biosignal acquisition unit 140. The biosignal acquisition unit 140 may be configured to acquire biosignal data, which may represent an eye activity. In this respect, the biosignal acquisition unit 140 may be arranged to register biopotentials based on muscle, skin or nerve activity in relation to eye activity.

Figure 2:
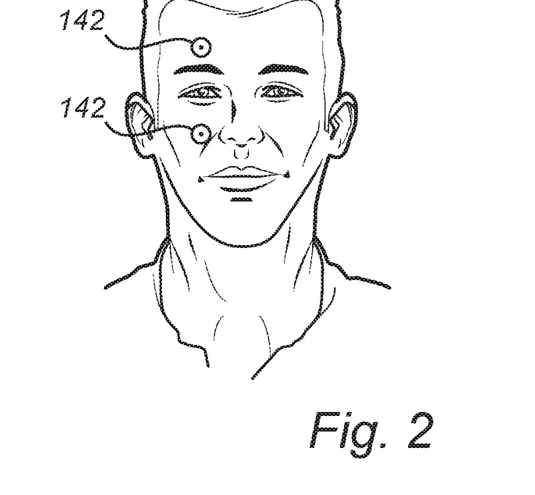
FIG. 2 is a view of a user illustrating placement of electrodes of for acquisition of biosignal data.

The biosignal acquisition unit 140 may comprise a set of skin electrodes 142 adapted to be arranged in an eye region of the user. The set of skin electrodes 142 may comprise a pair of skin electrodes 142, which are arranged above and below an eye, respectively, as illustrated in FIG. 2.

The eye acts as a dipole in which the positive pole is at the cornea and the negative pole is at the retina. A potential difference between the electrodes 142 may be representative of an arrangement of the eye dipole in relation to the skin electrodes 142. As will be further described below, the potential difference varies during an eye blink. Biosignal data acquired based on detecting an arrangement of the eye dipole in relation to the skin electrodes 142 may be called electrooculography (EOG) data.

The biosignal acquisition unit 140 may further comprise circuitry 144 connected to the set of skin electrodes 142 and arranged to measure the potential difference between the skin electrodes 142 and acquire the measured potential difference as biosignal data by sampling and digitizing the measured potential difference. Circuitry for measuring and acquiring of data of a potential difference is per se known in the art and will therefore not be further described herein.

The system 100 may further comprise a biosignal processing unit 150. The biosignal processing unit 150 may be configured to receive the biosignal data from the biosignal acquisition device 140.

The biosignal processing unit 150 may be configured to process the received biosignal data in order to detect closing of the eye. The biosignal processing unit 150 may thus comprise an algorithm for analyzing the biosignal data so as to determine when an eye is about to close or when the eye is closed.

The biosignal processing unit 150 may further be configured to process the received biosignal data in order to detect opening of the eye. The biosignal processing unit 150 may thus comprise an algorithm for analyzing the biosignal data so as to determine when an eye is about to open.

Figure 3:
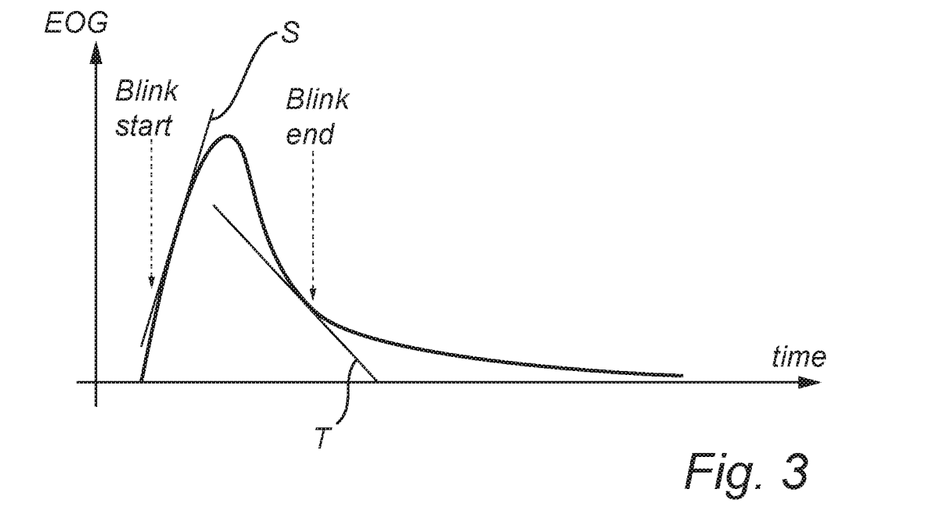
FIG. 3 is a chart illustrating biosignal data acquired by the system.

Reference is now made to FIG. 3, showing typical EOG data over time during a blink of an eye. The biosignal processing unit 150 may process EOG data for detecting blinks.

According to an algorithm, a derivative based on the EOG data may be analyzed.

Start of a blink may be detected by means of a first derivative computation. A slope S of the derivative is found and may be compared to a threshold, such that, when the slope S is above a threshold it may be concluded that a blink is starting. Alternatively, a machine learning algorithm may be used on the EOG data or the derivative based on EOG data to determine the blink start.

End of a blink may be detected by means of detecting a change of sign in a second derivative of the EOG data. Thus, a blink end may be detected at a point indicated by a tangential line T in the chart in FIG. 3. This may be detected by comparison to a threshold or by a machine learning algorithm as described above. Also, processing of biosignal data may be set such that detection of a blink end may not be done unless a blink start has first been detected.

Referring now again to FIG. 1, the system 100 may further comprise a control unit 160. The control unit 160 may be arranged to control an eye tracking process and all components involved in tracking of an eye position, as will be further described below. The control unit 160 may in particular be configured to respond to a detection of a closing of an eye by the biosignal processing unit 150. Since no meaningful image-based eye tracking may be performed during the time an eye is closed, the control unit 160 may thus be arranged to pause at least parts of an eye tracking process during blinks. The control unit 160 may be arranged to output a control signal for pausing one or more of an image capture operation by the image capturing device 110, an image processing operation of the image processing unit 120 and a transfer of data between the image capturing device 110 and the image processing unit 120. During the period of time that the biosignal processing unit 150 detects that images of the eye are not usable, the control unit 160 may provide a notification that no output data is available due to eye lid occlusion of the eye ball.

The control unit 160 may also be arranged to output a control signal for resuming or "un-pause" the eye tracking process. In this regard, the control unit 160 may comprise or maintain a timer 162, which may be used for enabling time-based control of resuming the eye tracking process. The control unit 160 may also or alternatively be configured to respond to a detection of an opening of an eye by the biosignal processing unit 150 for resuming the eye tracking process. The control unit 160 may in this regard be arranged to output a control signal for returning paused operations to an active state, i.e. to the paused one or more of an image capture operation by the image capturing device 110, an image processing operation of the image processing unit 120 and a transfer of data between the image capturing device 110 and the image processing unit 120.

Each of the image processing unit 120, the biosignal processing unit 150 and the control unit 160 may be implemented as any unit being capable of performing processing of data. The unit may be implemented as a dedicated processing unit including circuitry dedicated to perform the functions of the processing unit. The circuit may be a digital logic circuit. The circuit may be implemented in an integrated circuit such as a chipset. The circuit may also be implemented in a field programmable gate array (FPGA) or an application specific integrated circuit (ASIC). The unit may also be implemented in a general-purpose processing unit, such as a microprocessor, e.g. a central processing unit (CPU), which may be provided with a set of software instructions for performing the processing operations.

The image processing unit 120, the biosignal processing unit 150 and the control unit 169 may be implemented in a common unit, such as a microprocessor running different processes for handling the processing of the respective units. As an alternative, the image processing unit 120, the biosignal processing unit 150 and the control unit 160 may be implemented as separate units.

The system 100 may be arranged as a self-contained unit on a head-mounted structure. All components of the system 100 as described above may thus be arranged in a common and compact housing 102. This implies that the system 100 may be manufactured and delivered as a separate, self-contained unit, which may later be installed or integrated in or on a head-mounted structure, such as goggles, which may be separately manufactured (even at a different location from manufacturing of the system 100). For instance, the housing 102 may be attached to or mounted on frames of goggles or other eyewear to be worn by a user.

It is possible that the image processing unit 120 may be arranged separately from the other components of the system, as also mentioned above.

For instance, the image processing unit 120 may be arranged in a portable computing device, which may also be carried or worn by the user, such as in a mobile phone or a tablet computer. This implies that the possibly computing-expensive image processing need not be arranged in a housing 102 to be integrated in a head-mounted structure, which may be beneficial to keep down weight and size of the housing 102.

Figure 4:
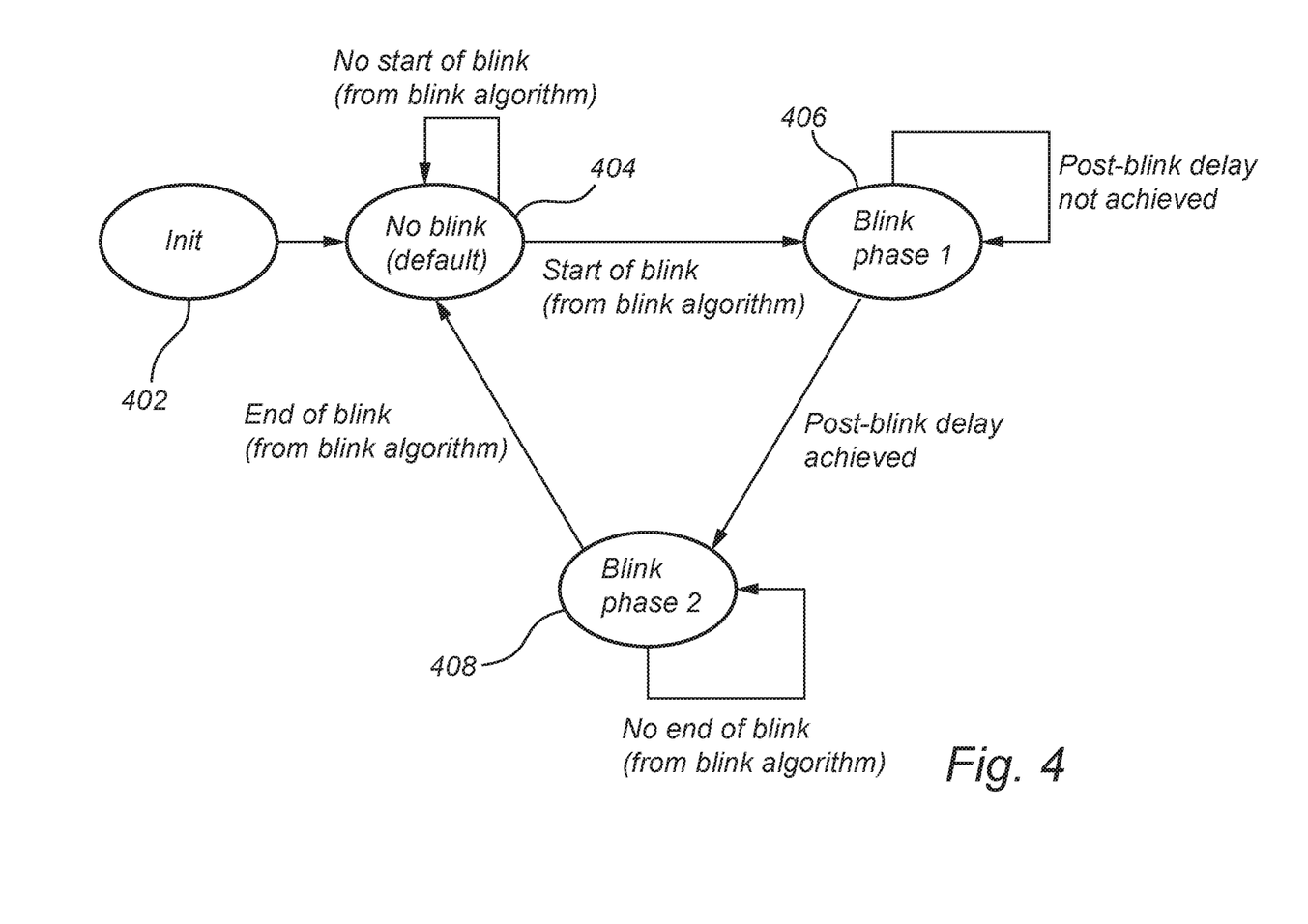
FIG. 4 is a state diagram illustrating states of the system.

Referring now to FIG. 4, control of the eye tracking process will be further described. The control unit 160 may implement a state machine controlling states of the eye tracking process. The control unit 160 may receive input from the biosignal processing unit 150 in order to control the states of the eye tracking process.

The control unit 160 may start the system 100 in an init state, 402. In this state, the image capturing device 110 may run an optional self-test, and start the acquisition of images. Further, the biosignal acquisition unit 140 may initialize the EOG data acquisition. Also, the image processing unit 120 may initialize an image processing algorithm and the biosignal processing unit 160 may initialize an EOG data processing algorithm. As soon as all initialization is complete, the state may transition to a "no blink" state 404.

The "no blink" state 404 is a default, active state of the system 100. By default the system 100 will be acquiring images, processing images and reporting eye-related features computed from the images. The features may e.g. be reported to an external unit, such as for enabling a human-machine interface based on eye movements. Alternatively or additionally, the features may be stored in a memory of the system 100 in order to log recorded eye movements. By extracting features, i.e. identifying and/or determining positions of features whose position on the eye ball is static or fixed, an orientation of the eye ball with respect to a fixed reference may be determined.

Simultaneously, the biosignal acquisition unit 140 acquires biosignal data and the biosignal processing unit 150 processes the biosignal data in order to detect closing of the eye. For example, the acquiring and processing of biosignal data may be performed during the image capturing, outputting of images to the image processing unit 120 and processing of the images, in the sense of being time duplexed or performed in parallel.

When the biosignal processing unit 150 detects the closing of the eye, the biosignal processing unit 150 may provide an external signal to the control unit 160 flagging the start of a blink. Then, the control unit 160 may thus output a control signal that ensures that the system 100 transitions state to a paused state 406, which is called "blink phase 1" state below. As long as the biosignal processing unit 150 has not detected the closing of the eye or start of a blink, the system 100 remains in the "no blink" state 404.

When the eye is closing or is already closed, the image-based eye tracking process will not be able to determine positions of the eye (as for instance the pupil and iris are not visible in acquired images). Hence, the control unit 160 may pause the eye tracking process in order to save processing power and memory. Thus, the control unit 160 may output a control signal in order for the system 100 to enter "blink phase 1" state.

In the "blink phase 1" state, the system 100 may be arranged to use minimal power. Thus, in "blink phase 1" state, the image capturing device 110 may stop image acquisition and the image processing unit 120 may stop image processing. Also, transfer of data, including a sequence of acquired images may be stopped between the image capturing device 110 and the image processing unit 120. This may be particularly relevant when the image processing unit 120 is arranged remotely to the image capturing device 120 and a transmitter 130 performs wireless communication with an external unit in which the image processing unit 120 is arranged. When the image processing unit 120 no longer receives images, it may also stop image processing.

The system 100 may report default values for features which are pre-defined for the paused state 406, e.g. using look-up in a table. For instance, the default values may be stored in a log of a sequence of eye positions to indicate eye blinks in the log.

The control unit 160 may use the timer 162 in order to determine a time delay after the detection of the closing of the eye. This time delay may be calibrated or a default value may be used that is based on a typical duration of an eye blink. For instance, eye blinks may have an average duration of 300-400 ms. The time delay may be shorter than the average duration of an eye blink such that the system 100 is able to be put in the active state 402 before the eye is opened. Thus, after a predetermined time delay has elapsed, the control unit 160 may output a control signal for transitioning the paused processes to a waiting state 408, which is called "blink phase 2" state below. As long as the predetermined time delay has not elapsed, the system 100 remains in the "blink phase 1" state 406.

In the "blink phase 2" state 408, the end of the blink should be close. The "blink phase 2" state 408 may be used for preparing the system 100 for the re-start of the eye tracking process, so that by the time the end of blink is detected, the eye tracking process can be quickly resumed, or the system 100 can already perform its regular activities in the "no blink" state 404.

Thus, the image capturing device 110 may power up the image sensor circuitry so that image capturing device 110 may be arranged in a "ready" condition to start accumulating charges based on incoming light and converting the received light to digital images. The transition to the "ready" condition may further include the image capturing device 110 setting the exposure level and/or acquiring focus.

The outputting of data may be prepared by clearing and/or allocating storage areas for image data and/or initializing and/or reserving a data bus for communication with the image processing unit 120. When a transmitter 130 is used for communication with a remotely arranged image processing unit 120, the transmitter 130 may be powered up and a communication link with the external unit, in which the image processing unit 120 is arranged, may be established.

The image processing unit 120 may be prepared by initializing registers, variables and/or control loops used for the processing of images.

The amount of time in the "blink phase 2" state 408 may be determined by the time delay previously discussed, i.e. a timing of when the "blink phase 2" state 408 is entered may be controlled by the time delay. The time delay could be calibrated using a conservative value of average durations of blinks and cross-referencing it against an amount of time the system 100 takes to wake up and be ready to resume the eye tracking process.

The control unit 160 may maintain the system 100 in the "blink phase 2" state 408 as long as no signal flagging the end of the blink is received. When the control unit 160 receives a signal from the biosignal processing unit 150 indicating the end of the blink, the control unit 160 may output a control signal returning the system 100 back to the "no blink" state 404.

The control unit 160 may be arranged to cause transition between states based on other combinations of input. For instance, once a detection of the closing of the eye is made and the system 100 is arranged in the paused state 404, the control unit 160 may only use the timer 162 in order to determine when to resume the eye tracking process.

It is possible to use the timer 162 for determining a first time delay, based on calibration and/or knowledge of average duration of blinks. Thus, when the first time delay has elapsed, the control unit 160 may cause the system 100 to enter the waiting state 408. Then, the timer 162 may be used for determining a second time delay, subsequent to the first time delay, and when the second time delay has elapsed the control unit 160 may cause the system 100 to enter the active state 404.

As an alternative, the system 100 may enter the init state 402 after the first time delay has elapsed and may then be automatically returned to the active state 404 once the system 100 is ready to perform the eye tracking process.

According to a further alternative, the transition from the paused state 406 to the active state 404 may be based on detection of the opening of the eye by the biosignal processing unit 150. Thus, when the biosignal processing unit 150 detects that the eye is about to open, the control unit 160 may output a control signal for resuming the eye tracking process by returning directly from the paused state 406 to the active state 404.

Figure 5:
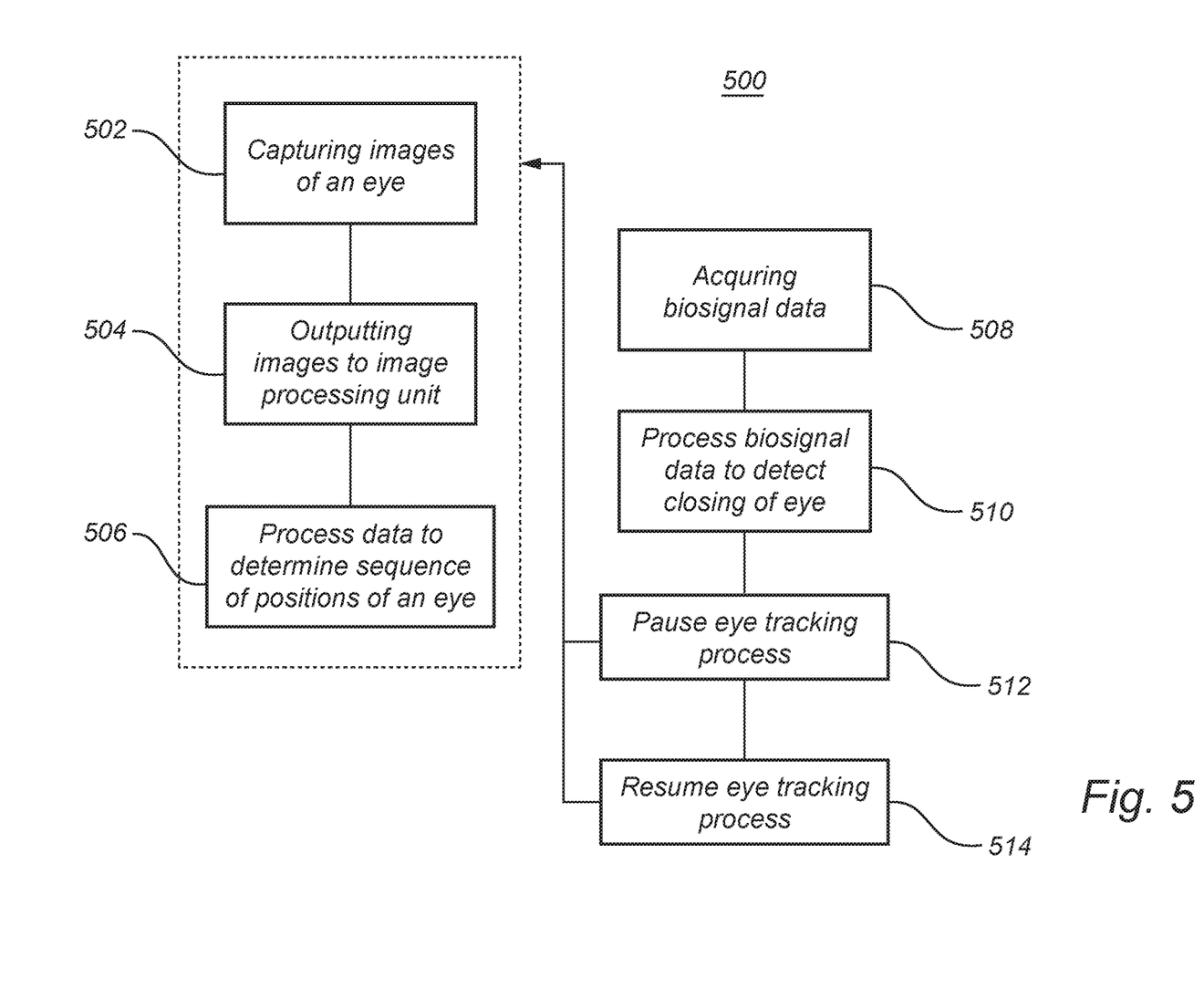
FIG. 5 is a flow chart illustrating a method for image-based eye tracking.

Referring now to FIG. 5, a method 500 for eye tracking will be described.

The method comprises performing an eye tracking process in order to obtain a sequence of eye positions, sizes and orientations. The eye tracking process may comprise capturing, step 502, a sequence of digital images of an eye of a user. The eye tracking process further comprises outputting, step 504, data including the sequence of images to an image processing unit 120. The image processing unit 120 then processes, step 506, the data to determine a sequence of positions of the eye, wherein each position is indicative of a gaze direction and other features such as pupil size are indicative of physiological or psychological events of the user.

The method further comprises, during the eye tracking process (e.g. in parallel with the eye tracking process or time duplexed with the eye tracking process), acquiring, step 508, biosignal data representing an activity of the eye. The acquired biosignal data is processed, step 510, to detect a closing of an eye, which would prevent the image based eye tracking process to keep track of the eye while the eye is closed.

In response to detecting the closing of the eye, the eye tracking process is paused, step 512, in that at least one of the capturing 502, outputting 504 and processing 506 is paused.

The eye tracking process may be resumed, step 514, in response to a pre-determined time delay having elapsed and/or the detection of the opening of the eye by the biosignal data processing 510.

A variation of method in FIG. 5 is applicable also to a post-processing scenario wherein steps corresponding to steps 502, 508 and 510 are performed in parallel or in a time duplexed manner. The captured images and the acquired biosignal data may be output to a computing device for a post-processing eye tracking process. During the post-processing, the captured images and the acquired biosignal data may be processed in parallel such that the biosignal data is synchronized with a currently analyzed image. In response to detecting closing of the eye based on the biosignal data processing, the image processing may accordingly be paused and remain paused in response to a pre-determined time delay having elapsed, or a predetermined number of image frames have been skipped, and/or the detection of the opening of the eye by the biosignal data processing.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for eye tracking, the method comprising:
capturing a sequence of digital images of an eye of a user;
outputting data including said sequence of images to an image processing unit;
processing said data by the image processing unit to determine a sequence of positions of the eye, each position being indicative of a gaze direction,
acquiring biosignal data representing an activity of the eye;
in response to detecting closing of the eye based on the acquired biosignal data, pausing said capturing; and
returning of said capturing to an active state from the paused state,
wherein returning of said capturing to the active state includes transitioning said capturing from the paused state to a waiting state and transitioning said capturing from the waiting state to the active state.

2. The method according to claim 1, wherein said act of transitioning from the paused state to the waiting state is performed after a preset time delay from said act of pausing.

3. The method according to claim 1, wherein said transitioning from the waiting state to the active state is performed in response to detecting opening of the eye based on the acquired biosignal data.

4. The method according to claim 1, wherein said returning to an active state is performed in response to detecting opening of the eye based on the acquired biosignal data.

5. The method according to claim 1, wherein said returning to an active state is performed after a preset time delay from said pausing.

6. A system for eye tracking, the system comprising:
an image capturing device configured to capture a sequence of digital images of an eye;
an image processing unit configured to receive data including said sequence of images from the image capturing device, and determine a sequence of positions of the eye, each position being indicative of a gaze direction;
a biosignal acquisition unit configured to acquire biosignal data representing an activity of the eye;
a biosignal processing unit configured to receive the biosignal data and detect closing of the eye based on the acquired biosignal data; and
a control unit configured to, in response to the biosignal processing unit detecting closing of the eye, output a control signal for pausing an image capture operation of the image capturing device,
wherein the control unit is further configured to output at least one control signal, wherein the image capture operation is returned to an active state from the paused state,
wherein the control unit is further configured to output:
a first control signal for transitioning the image capture operation in the paused state, to a waiting state; and
a second control signal for transitioning the image capture operation in the waiting state, to the active state.

7. The system according to claim 6, wherein the control unit is configured to output the first control signal after a preset time delay from said output of the control signal for pausing.

8. The system according to claim 6, wherein the control unit is configured to output the second control signal in response to the biosignal processing unit detecting opening of the eye based on the acquired biosignal data.

9. The system according to claim 6, wherein the control unit is configured to output said at least one control signal after a preset time delay from said output of the control signal for pausing or in response to the biosignal processing unit detecting opening of the eye based on the acquired biosignal data.

10. The system according to claim 6, further comprising a structure adapted to be head-mounted on a user, wherein the image capturing device and the biosignal acquisition unit are supported by the structure.

11. The system according to claim 6, wherein the biosignal acquisition unit includes a set of skin electrodes adapted to be arranged in an eye region of a user.

12. The method according to claim 1, further comprising:
in response to detecting closing of the eye based on the acquired biosignal data, pausing at least one of said outputting or said processing.

13. The method according to claim 12, further comprising:
returning to an active state at least one of said capturing, said outputting or said processing from the paused state.

14. The system according to claim 6, wherein the control unit is further configured to, in response to the biosignal processing unit detecting closing of the eye, output a control signal for pausing at least one of: an image processing operation of the image processing unit, or a transfer of data including said sequence of images between the image processing unit and the image capturing device.

15. The system according to claim 14, wherein the control unit is further configured to output at least one control signal, wherein at least one of the image processing operation or the transfer of data is returned to an active state from the paused state.

16. The system according to claim 15, wherein the control unit is further configured to output:
a first control signal for transitioning at least one of the image capture operation, the image processing operation, or the transfer of data, in the paused state to a waiting state; and
a second control signal for transitioning at least one of the image capture operation, the image processing operation, or the transfer of data, in the waiting state, to the active state.

* * * * *